United States Patent
Peters

(10) Patent No.: US 12,412,660 B2
(45) Date of Patent: *Sep. 9, 2025

(54) COMPUTER-IMPLEMENTED SYSTEM AND METHOD FOR CREATING GENERATIVE MEDICINES FOR DEMENTIA

(71) Applicant: FITZCARRALDO AB, Domsten (SE)

(72) Inventor: Filip Ludwig Peters, Domsten (SE)

(73) Assignee: FITZCARRALDO AB, Domsten (SE)

( * ) Notice: Subject to any disclaimer, the term of this patent is extended or adjusted under 35 U.S.C. 154(b) by 863 days.

This patent is subject to a terminal disclaimer.

(21) Appl. No.: 17/182,128

(22) Filed: Feb. 22, 2021

(65) Prior Publication Data

US 2021/0407673 A1 Dec. 30, 2021

Related U.S. Application Data

(63) Continuation-in-part of application No. 16/946,679, filed on Jun. 30, 2020, now Pat. No. 11,049,605.

(51) Int. Cl.

| | |
|---|---|
| *A61B 5/00* | (2006.01) |
| *G01N 21/77* | (2006.01) |
| *G06N 3/045* | (2023.01) |
| *G06N 3/088* | (2023.01) |
| *G16B 40/00* | (2019.01) |

(Continued)

(52) U.S. Cl.
CPC ............ *G16H 50/20* (2018.01); *G01N 21/77* (2013.01); *G06N 3/045* (2023.01); *G06N 3/088* (2013.01); *G16B 40/00* (2019.02); *G16H 10/20* (2018.01); *G16H 10/40* (2018.01); *G16H 10/60* (2018.01); *G16H 20/10* (2018.01); *G16H 20/60* (2018.01); *G16H 40/20* (2018.01); *G16H 40/67* (2018.01);

(Continued)

(58) Field of Classification Search
CPC ........ G16H 50/20; G16H 10/20; G16H 10/40; G16H 10/60; G16H 20/10; G16H 20/60; G16H 40/20; G16H 40/67; G16H 50/50; G16H 50/70; G16H 70/40; G16H 70/60; G01N 21/77; G06N 3/045; G06N 3/088; G16B 40/00

See application file for complete search history.

(56) References Cited

U.S. PATENT DOCUMENTS

| | | | |
|---|---|---|---|
| 2013/0338453 A1* | 12/2013 | Duke ..................... | A61B 5/486 600/309 |
| 2020/0027557 A1* | 1/2020 | Karow .................. | G16H 50/50 |

(Continued)

*Primary Examiner* — Maroun P Kanaan
(74) *Attorney, Agent, or Firm* — Silver Legal LLC; Jarrett L. Silver

(57) ABSTRACT

Computer-implemented systems and methods for creating generative medicines for dementia. The computer-implemented system includes a processor, a memory, and a server. The processor is configured to register a user over a communication application through a registration module; receive patient data of a user through a patient data module; receive bio-sample data of the user through a bio-sample module; receive dementia type and dementia severity data of the user through a dementia categorization module; and transmit a final dataset through a data transmission module. The server is configured to process the final dataset received from the data transmission module by applying a machine learning module; select the generative medicines; and transmit the generative medicines to the computing devices.

26 Claims, 6 Drawing Sheets

(51) Int. Cl.
*G16H 10/20* (2018.01)
*G16H 10/40* (2018.01)
*G16H 10/60* (2018.01)
*G16H 20/10* (2018.01)
*G16H 20/60* (2018.01)
*G16H 40/20* (2018.01)
*G16H 40/67* (2018.01)
*G16H 50/20* (2018.01)
*G16H 50/50* (2018.01)
*G16H 50/70* (2018.01)
*G16H 70/40* (2018.01)
*G16H 70/60* (2018.01)

(52) U.S. Cl.
CPC ............ *G16H 50/50* (2018.01); *G16H 50/70* (2018.01); *G16H 70/40* (2018.01); *G16H 70/60* (2018.01)

(56) References Cited

U.S. PATENT DOCUMENTS

2022/0073986 A1* 3/2022 Nalls .................. G16B 40/00
2022/0270711 A1* 8/2022 Feala .................. G16B 45/00

* cited by examiner

COMPUTER-IMPLEMENTED SYSTEM AND METHOD FOR CREATING GENERATIVE MEDICINES FOR DEMENTIA

CROSS-REFERENCES TO RELATED PATENT APPLICATIONS

This application is a continuation-in-part of U.S. patent application Ser. No. U.S. Ser. No. 16/946,679, filed Jun. 30, 2020, which are incorporated herein by reference in its entirety.

BACKGROUND

Technical Field

The invention presented herein is generally directed towards a computer-implemented system and method for creating generative medicines for dementia. More particularly, but not limited to, a computer-implemented system and method for creating generative medicine for dementia including but not limited to Alzheimer's disease, frontotemporal dementia, Lewy Body disease (LBD), early-onset dementia, and/or vascular dementia by applying adaptive and generative machine learning.

Description of the Related Art

Artificial intelligence (AI) and machine learning (ML) has the potential to save the lives of current and future patients and is something that is starting to be seen across healthcare services across the world. With ever-larger computational powers, an understanding of the possibilities of machine learning, and the growth of mobile technology in society, the ability to cost-efficiently collect patient data and provide personalized healthcare has reached an important point. Insights into the complex interplay between how lifestyle, genetics, biological reactions such as gut microbiomes, may affect dementia need to be further explored with machine learning tools that are becoming more advanced. Many of such factors may have been partially overlooked in the existing approaches to cure and prevent dementia. With the failure to develop dementia treatments and with dementia expected to double within the next 30 years, new approaches to developing dementia medicines are needed.

Alzheimer's and dementia have become a priority for the Food and Drug Administration (FDA). At the same time, 99% of trials in the past 20 years have failed. Alzheimer's disease discovery Foundation (ADDF) has stopped funding research based on the Amyloid beta hypothesis and is encouraging the pursuit of novel approaches to treating and/or preventing the disease. Millions of people worldwide are today given medications that may not help them. The ten most sold drugs in the United States help somewhere between 1 in 25 and 1 in 4 of the people that take them. For drugs such as statins which may be used to lower cholesterol, as few as 1 in 50 may benefit. Some drugs may even be harmful to certain ethnic groups stemming from a bias towards white Western participants in many of the clinical trials that have been conducted historically.

Personalized medicine is becoming increasingly important with several government bodies and life-sciences funding institutions globally increasingly supporting targeted treatment and patient engagement approaches in medicine, such as through the US Patient-Centred Outcomes Research Institute, established in 2010, and NIH's Precision Medicine Initiative. Personalized medicine today however is expensive, many times fails to be truly personal, and is often simply an adjustment of dosage of pre-existing medicine.

There are several problems with current approaches to finding a treatment for dementia. There may be unidentified factors in addition to the common Amyloid-beta and Tau protein presence that may be causing the disease. This may make medicine only targeting these two proteins ineffective in treating some patients. Dementia, including Alzheimer's disease, are furthermore diseases that manifest themselves over long periods. Differences in the severity of disease and different stages of the disease in patients may, therefore, impact the type of treatment that is necessary and may be inhibiting current approaches towards finding a treatment for the disease. The biological makeup of patients from biological samples (bio-samples) which may include data pertaining to the genetics, proteome, metabolome, and lipidome of the patient are known to impact the treatment receptibility of patients and may severely limit the "one medicine fits all" approaches being undertaken by many pharmaceutical developers within the research space. As is the case in many pharmaceutical development pursuits, rodent studies are typically employed in the molecule discovery process. In the case of dementia, which does not occur naturally in mice, specific genetic mutations are introduced to induce dementia-like manifestations in the process. Basing efficacy data off such mutations may not translate well into efficacy in human subjects. Another challenge arising from the use of mice in the identification of promising compounds for the treatment and/or prevention of dementia may be differences in telomere length between different mice populations. There is evidence to suggest that the telomere length of bred mice in laboratories is longer than the telomere length of mice that can be found in the wild. Studies based on mice where abnormally long telomeres are present may, therefore, bias the efficacy studies of early trials. It has furthermore been shown that reduced telomere length in humans may be positively associated with dementia. There may, therefore, be compounds that fail to show efficacy in the pre-discovery and discovery processes of clinical research, which may be helpful for human subjects in the fight against dementia.

Although there has been some focus on applying machine learning methods in the primary stages of the medicine development, e.g., in the molecular generation parts of the pre-discovery and discovery processes of drug development, AI and machine learning applications in dementia research are limited by the fact that there have been few successes in the discovery of appropriate molecules for the treatment and/or prevention of dementia. There is consequently no data that machine learning methods can learn from and the research space has consequently been unable to realize the full potential of machine learning tools in this setting.

Therefore, there is a need for a computer-implemented system and method for creating affordable personalized medicines for dementia that leverage generative machine learning tools and adaptive research settings to create affordable and truly personalized healthcare.

Thus, in view of the above, there is a long-felt need in the healthcare industry to address the aforementioned deficiencies and inadequacies.

SUMMARY

Computer-implemented systems and methods for creating generative medicines for dementia are provided, as shown in and/or described in connection with at least one of the figures.

One aspect of the present disclosure relates to a computer-implemented method for creating one or more generative medicines for dementia. The computer-implemented method includes a step of registering a user over a communication application by receiving one or more credentials from the user for providing access to the communication application through a registration module. The computer-implemented method includes a step of receiving patient data of a user through a patient data module. The computer-implemented method includes a step of receiving bio-sample data of the user through a bio-sample module. The computer-implemented method includes a step of receiving dementia type and dementia severity data of the user through a dementia categorization module. The computer-implemented method includes a step of transmitting a final dataset by compiling the patient data, the bio-sample data, the dementia type, and dementia severity data, and the dementia progression data of the user through a data transmission module. The computer-implemented method includes a step of processing the final dataset by applying a machine learning module to the final dataset received from the data transmission module over a network. The machine learning module has been trained to create generative medicines based on the progression of dementia of the user using a generative adversarial neural network (GAN). The GAN includes one or more Deep Convolutional GANs (DCGANs), one or more Wasserstein GANs (WGANs), and one or more Self-Attention GANs (SAGANs). The computer-implemented method includes a step of selecting the one or more generative medicines created by the machine learning module with the highest expected efficacy for treatment or prevention of dementia, or any combination of treatment or prevention of mental health disorders based on the machine learning module. The computer-implemented method includes a step of transmitting the generative medicines to one or more computing devices.

In an embodiment, the bio-sample module is configured to facilitate the user to collect a bio-sample from salivary glands in a form of saliva.

In an embodiment, the bio-sample module is configured to facilitate the user to place the bio-sample on a reactant material having one or more reactant properties pertaining to biological and/or chemical information of the user's body.

In an embodiment, the bio-sample module is configured to facilitate the user to capture an image of the reactant material upon placing the bio-sample to obtain the bio-sample data.

In an embodiment, the communication application is executable on one or more computing devices of the user.

In an embodiment, the server generates one or more tailored diets based on the final dataset processed by the machine learning module.

In an embodiment, the server estimates the toxicity of the generative medicines transmitted to the computing device through a toxicity estimation module.

In an embodiment, the one or more processors are configured to collect genetic data of the user through a genetic data module.

In an embodiment, the generated medicines may be produced and provided to the patients.

In an embodiment, the neuronal activity of the user may be collected through a neuronal activity data module. Such collections of data may include methods but are not limited to Functional Magnetic Resonance Imaging (fMRI), Calcium Imaging, Electroencephalography (EEG) and Electrocorticography (ECoG).

The measurement of neuronal activity may furthermore comprise the collection of any collection of information on the blood flow in the brain. It is well known that the relative presence of oxygenated versus deoxygenated blood is an indication of neuronal activity as active brain regions require more oxygenated blood, with the possibility of inferring activity patterns of neurons.

The measurement of neuronal activity may furthermore comprise the collection of any electrical activity from the brain of the subject. It is well known that the electrical activity of a head can be viewed as the summed activity of hundreds of thousands or millions of neurons in the form of oscillatory activity and that different frequencies of oscillation correlates with different behavioural states. Such electrical activity may be measure invasively or non-invasively.

An aspect of the present disclosure relates to a computer-implemented system for creating generative medicines for dementia. The computer-implemented system includes a processor, a memory, and a server. The memory is configured to register a user over a communication application by receiving one or more credentials from the user for providing access to the communication application through a registration module; receive patient data of a user through a patient data module; receive bio-sample data of the user through a bio-sample module; receive dementia type and/or dementia severity data of the user through a dementia categorization module; and transmit a final dataset by compiling the patient data, the bio-sample data, the dementia type, and dementia severity data, and the dementia progression data of the user through a data transmission module. The server is communicatively coupled to the memory over a network. The server is configured to process the final dataset received from the data transmission module over a network by applying a machine learning module. The machine learning module has been trained to create generative medicines based on the progression of dementia of the user using a generative adversarial neural network (GAN). The GAN comprising one or more Deep Convolutional GANs (DCGANs), one or more Wasserstein GANs (WGANs), and one or more Self-Attention GANs (SA-GANs). The server is configured to select, the one or more generative medicines created by the machine learning module, the one or more generative medicines with the highest expected efficacy for treatment or prevention of dementia is selected, or any combination of treatment or prevention of mental health disorders based on the machine learning module. The server is configured to transmit the one or more generative medicines to one or more computing devices.

In an embodiment, the bio-sample module is configured to facilitate the user to collect a bio-sample from salivary glands in a form of saliva.

In an embodiment, the bio-sample module is configured to facilitate the user to place the bio-sample on a reactant material having one or more reactant properties pertaining to chemical information of the user's body.

In an embodiment, the bio-sample module is configured to facilitate the user to capture an image of the reactant material upon placing the bio-sample to obtain the bio-sample data.

In an embodiment, the communication application is executable on the computing devices of the user.

In an embodiment, the server generates one or more tailored diets based on the final dataset processed by the machine learning module.

In an embodiment, the server estimates the toxicity of the generative medicines transmitted to the computing device through a toxicity estimation module.

In an embodiment, the one or more processors are configured to collect genetic data of the user through a genetic data module.

An aspect of the present disclosure relates to a computer-implemented method for creating one or more generative medicines for dementia. The computer-implemented method includes a step of registering, by one or more processors, a user over a communication application by receiving one or more credentials from the user for providing access to the communication application through a registration module. The method includes a step of receiving, by the one or more processors, patient data of the user through a patient data module. The method includes a step of transmitting, by the one or more processors, a final dataset by compiling the data related to the user through a data transmission module. The method includes a step of processing, by a server, the final dataset received from the data transmission module over a network by applying a machine learning module. The machine learning module is configured to generate features from the final dataset by interrelating the user's data and the generative medicine data. The computer-implemented method includes a step of creating, by the server, the one or more new generative medicines based on the processed dataset by the machine learning module. The server creates the generative medicines for treatment or prevention of dementia, or any combination of treatment or prevention of dementia based on the final dataset processed by the machine learning module. The machine learning module has been trained to predict the progression of dementia and is configured to generate a new dataset by adjusting the medical recipe values in each generative medicine using an optimization algorithm that optimizes for values that generate the highest predicted efficacy by the machine learning module. The server employs an optimization algorithm to create the generative medicines based on the user's data. The optimization algorithm comprises one or more population algorithms, direct algorithms and stochastic algorithms. The computer-implemented method includes a step of selecting, the one or more generative medicines with the highest predicted efficacies on the progression of dementia of the user. The computer-implemented method includes a step of transmitting, by the server, the one or more generative medicines to one or more computing devices of the user.

In an embodiment, the machine learning model is trained using the progression of dementia as a y-variable that is being optimized. This progression of dementia may be measured over any period of time that can be expected to reliably produce accurate measures of dementia progression.

In an embodiment, the machine learning model is trained using the progression of dementia as measured from animals.

In an embodiment, the invention may be applied to generating personalized medicines for animals.

In an embodiment, the step of receiving the patient data includes a step of receiving, by the one or more processors, at least one of or any combination of bio-sample data of the user through at least one bio-sample module; and mental health questionnaire data from the user through a questionnaire module.

In an embodiment, the step of transmitting the final dataset by compiling the data related to the user through a data transmission module includes a step of compiling one of or any combination of the bio-sample data, and the mental health questionnaire data of the user through the data transmission module. The one or more transmitted generative medicines are produced and sent to the user.

In an embodiment, each generative medicine's likelihood of overfitting is predicted by using a discriminator machine learning model.

Accordingly, one advantage of the present invention is that it provides a computer-implemented method and system for dementia assessment and personalized dementia medicine generation. Generative medicine or personalized medicine for dementia has the potential of being more accurate, with fewer side-effects.

Accordingly, one advantage of the present invention is that it provides a computer-implemented method and system that incorporate reminders, nudges, and notifications into the communication application to help the patient stick to their medicine which may enable the patient to be more inclined to adhere to their medication schedule and increase the efficacy of the medicine.

Accordingly, one advantage of the present invention is that it provides a computer-implemented method and system that can continuously track the patient's general wellbeing and progression of dementia.

Accordingly, one advantage of the present invention is that it provides a computer-implemented method and system that can enable decentralized dementia trials, reducing costs, and increasing the ability to increase patient sample sizes in trials.

Accordingly, one advantage of the present invention is that it utilizes a data-driven approach to provide robustness across patient cohorts in terms of objectivity and interpretability and may furthermore not be prone to environmental circumstances of clinical settings which may interfere with the communicative process between a clinician and a patient.

Accordingly, one advantage of the present invention is that it may incorporate safe natural health medicines into a personalized dementia treatment plan to provide safe medicine to patients.

Accordingly, one advantage of the present invention is that it may not require a pre-discovery, discovery, or pre-clinical process, and may discover appropriate treatments for patients in shorter amounts of time.

Accordingly, one advantage of the present invention is that it may produce valuable insight into how certain medical compounds affect patients' wellbeing.

Accordingly, one advantage of the present invention is that it employs machine-learning enabled image analysis to analyze one or more bio-samples which is beneficial for many reasons including that the bio-sample does not need to be transported far distances to a lab for analysis, which may increase the integrity of the bio-sample as there is less opportunity for the sample to be interfered with and interact with different environments.

Accordingly, one advantage of the present invention is that it reduces the time to predict potential symptom reducing medicines to reduce the prevalence of adverse events resulting from dementia.

Accordingly, one advantage of the present invention is that the severity of data leakage risks may be reduced. Typically, the microbiome is correlated with dementia. The microbiome can furthermore be found in bio-samples. Therefore, salivary bio-samples may have some correlation to rates of dementia. The bio-sample collection process of the present invention does not aim to sequence DNA or genome in a fashion that may be interpretable by outside parties but focuses on identifying characteristics pertaining to dementia, which leads to data that is more unique and usable for the described purpose herein. The severity of data leakage risks may, therefore, be reduced.

These features and advantages of the present disclosure may be appreciated by reviewing the following description of the present disclosure, along with the accompanying figures wherein like reference numerals refer to like parts.

BRIEF DESCRIPTION OF THE DRAWINGS

The accompanying drawings illustrate the embodiments of systems, methods, and other aspects of the disclosure. Any person with ordinary skills in the art will appreciate that the illustrated element boundaries (e.g., boxes, groups of boxes, or other shapes) in the figures represent an example of the boundaries. In some examples, one element may be designed as multiple elements, or multiple elements may be designed as one element. In some examples, an element shown as an internal component of one element may be implemented as an external component in another and vice versa. Furthermore, the elements may not be drawn to scale.

Various embodiments will hereinafter be described in accordance with the appended drawings, which are provided to illustrate, not limit, the scope, wherein similar designations denote similar elements, and in which.

DETAILED DESCRIPTION

The present description is best understood with reference to the detailed figures and description set forth herein. Various embodiments of the present system and method have been discussed with reference to the figures. However, those skilled in the art will readily appreciate that the detailed description provided herein with respect to the figures are merely for explanatory purposes, as the present system and method may extend beyond the described embodiments. For instance, the teachings presented and the needs of a particular application may yield multiple alternative and suitable approaches to implement the functionality of any detail of the present systems and methods described herein. Therefore, any approach to implement the present system and method may extend beyond certain implementation choices in the following embodiments.

According to an embodiment herein, the methods of the present invention may be implemented by performing or completing manually, automatically, and/or a combination of thereof. The term "method" refers to manners, means, techniques, and procedures for accomplishing any task including, but not limited to, those manners, means, techniques, and procedures either known to the person skilled in the art or readily developed from existing manners, means, techniques and procedures by practitioners of the art to which the present invention belongs. The persons skilled in the art will envision many other possible variations within the scope of the present system and method described herein.

Figure 1:
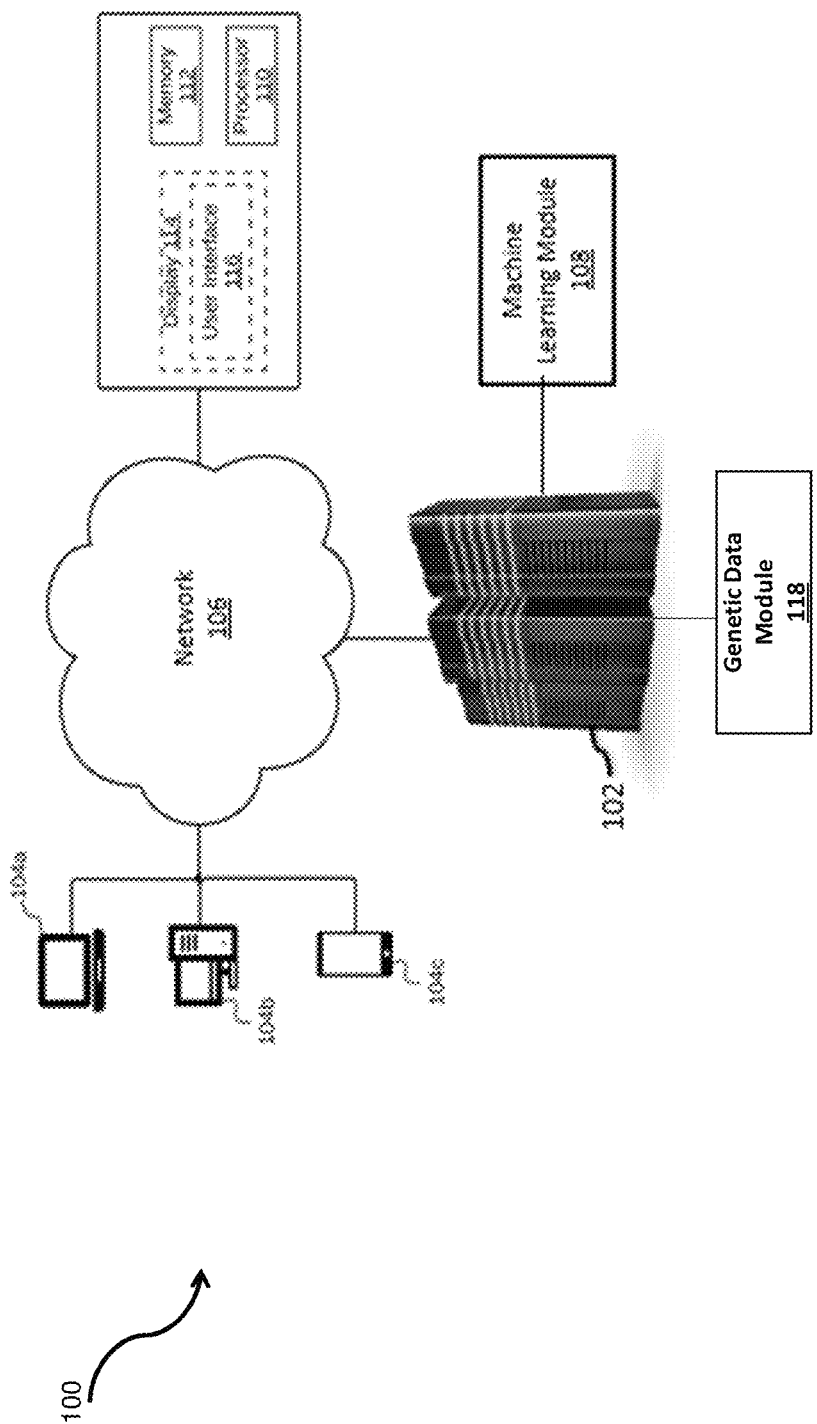
FIG. 1 illustrates a block diagram of the present computer-implemented system for creating generative medicines for dementia, in accordance with one embodiment of the present invention.

FIG. 1 illustrates a block diagram of the present computer-implemented system 100 for creating generative medicines for dementia, in accordance with one embodiment of the present invention. The computer-implemented system 100 includes a processor 110, a memory 112, and a server 102. The memory 112 is communicatively coupled to the processor 110, wherein the memory 112 stores instructions executed by the processor 110. The memory 112 may be a non-volatile memory or a volatile memory. Examples of non-volatile memory may include, but are not limited to flash memory, a Read Only Memory (ROM), a Programmable ROM (PROM), Erasable PROM (EPROM), and Electrically EPROM (EEPROM) memory. Examples of volatile memory may include but are not limited to Dynamic Random-Access Memory (DRAM), and Static Random-Access memory (SRAM).

The processor 110 may include at least one data processor for executing program components for executing user- or system-generated requests. Processor 110 may include specialized processing units such as integrated system (bus) controllers, memory management control units, floating point units, graphics processing units, digital signal processing units, etc. Processor 110 may include a microprocessor, such as AMD® ATHLON® microprocessor, DURON® microprocessor OR OPTERON® microprocessor, ARM's application, embedded or secure processors, IBM® POWERPC®, INTEL'S CORE® processor, ITANIUM® processor, XEON® processor, CELERON® processor or other line of processors, etc. Processor 110 may be implemented using mainframe, distributed processor, multi-core, parallel, grid, or other architectures. Some embodiments may utilize embedded technologies like application-specific integrated circuits (ASICs), digital signal processors (DSPs), Field Programmable Gate Arrays (FPGAs), etc.

Processor 110 may be disposed of in communication with one or more input/output (I/O) devices via an I/O interface. I/O interface may employ communication protocols/methods such as, without limitation, audio, analog, digital, RCA, stereo, IEEE-1394, serial bus, universal serial bus (USB), infrared, PS/2, BNC, coaxial, component, composite, digital visual interface (DVI), high-definition multimedia interface (HDMI), RF antennas, S-Video, VGA, IEEE 802.n/b/g/n/x, Bluetooth, cellular (e.g., code-division multiple access (CDMA), high-speed packet access (HSPA+), global system for mobile communications (GSM), long-term evolution (LTE), WiMax, or the like), etc.

The system 100 requires a user to register on a communication application configured within one or more computing devices 104 (for example, a laptop 104a, a desktop 104b, and a smartphone 104c). Other examples of the computing devices 104, may include but are not limited to a phablet and a tablet. A user may include a patient, a patient using the communication application using the computing devices 104 such as those included in this invention, or such a computing device itself. The processor 110, memory 112, server 102, and the computing devices 104 are communicatively coupled over a network 106. Network 106 may be a wired or a wireless network, and the examples may include but are not limited to the Internet, Wireless Local Area Network (WLAN), Wi-Fi, Long Term Evolution (LTE), Worldwide Interoperability for Microwave Access (WiMAX), and General Packet Radio Service (GPRS).

Memory 112 further includes various modules that enable the present computer-implemented system 100 for generating one or more tailored medical recipes for mental health disorders. These modules are explained in detail in conjunction with FIG. 2. The present computer-implemented system 100 may further include a display 114 having a User Interface (UI) 116 that may be used by the user or an administrator to initiate a request to view the tailored medical recipes and provide various inputs to the present computer-implemented system 100. In an embodiment, the User Interface (UI or GUI) 116 is a convenient interface for accessing the information related to the tailored medical recipes, including the patient data, the voice data, the bio-sample data, the face image data, and the mental health questionnaire data of the user. Display 114 may further be used to display tailored medical recipes to the users. The functionality of the computer-implemented system 100 may alternatively be configured within each of the plurality of computing devices 104.

Figure 2:
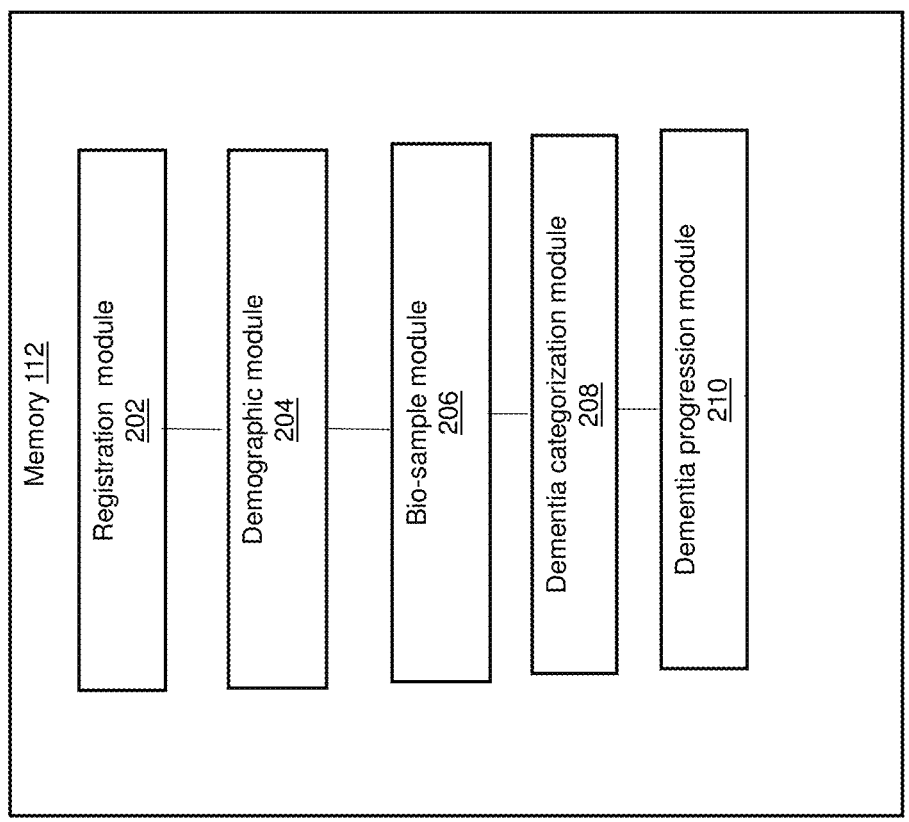
FIG. 2 illustrates a block diagram of the various modules within a memory of a computing device, in accordance with another embodiment of the present invention.

FIG. 2 illustrates a block diagram of the various modules within a memory 112 of a computing device 104, in accordance with another embodiment of the present invention. FIG. 2 is explained in conjunction with FIG. 1. The memory 112 includes a registration module 202, a patient data module 204, a bio-sample module 206, a dementia categorization module 208, and a data transmission module 210. These modules are software components or part of a program that contains one or more routines.

The memory 112 is configured to register a user over a communication application by receiving one or more credentials from the user for providing access to the communication application through a registration module 202. Examples of the credentials including but not limited to a user name, password, age, gender, phone number, email address, location, etc. In an embodiment, the communication application is executable on the computing devices 104 of the user and implemented on one or more operating systems such as Android®, iOS®, Windows®, etc. In an embodiment, the communication application is commercialized as an application for creating personalized medicine for dementia which is a software application, or a mobile application, or a web application.

The memory 112 is configured to receive patient data pertaining to the user through a patient data module 204. In an embodiment, the user is prompted to enter his/her patient data. Patient data such as gender, ethnicity, weight, height, sleeping habits, and previous medical history may be important in determining the efficacy of personalized medicine. Patient data may further comprise information about the patient's genes and/or presence of diseases that may correlate with dementia progression. Such genetic information may include but is not limited to Presenilin 1 (PSEN1), Presenilin 2 (PSEN2), and the Amyloid Precursor Protein (APP) gene. The presence of certain types of diseases that may correlate with dementia progression may include but is not limited to gum disease or any other bacterial, inflammatory or viral diseases.

Figure 3:
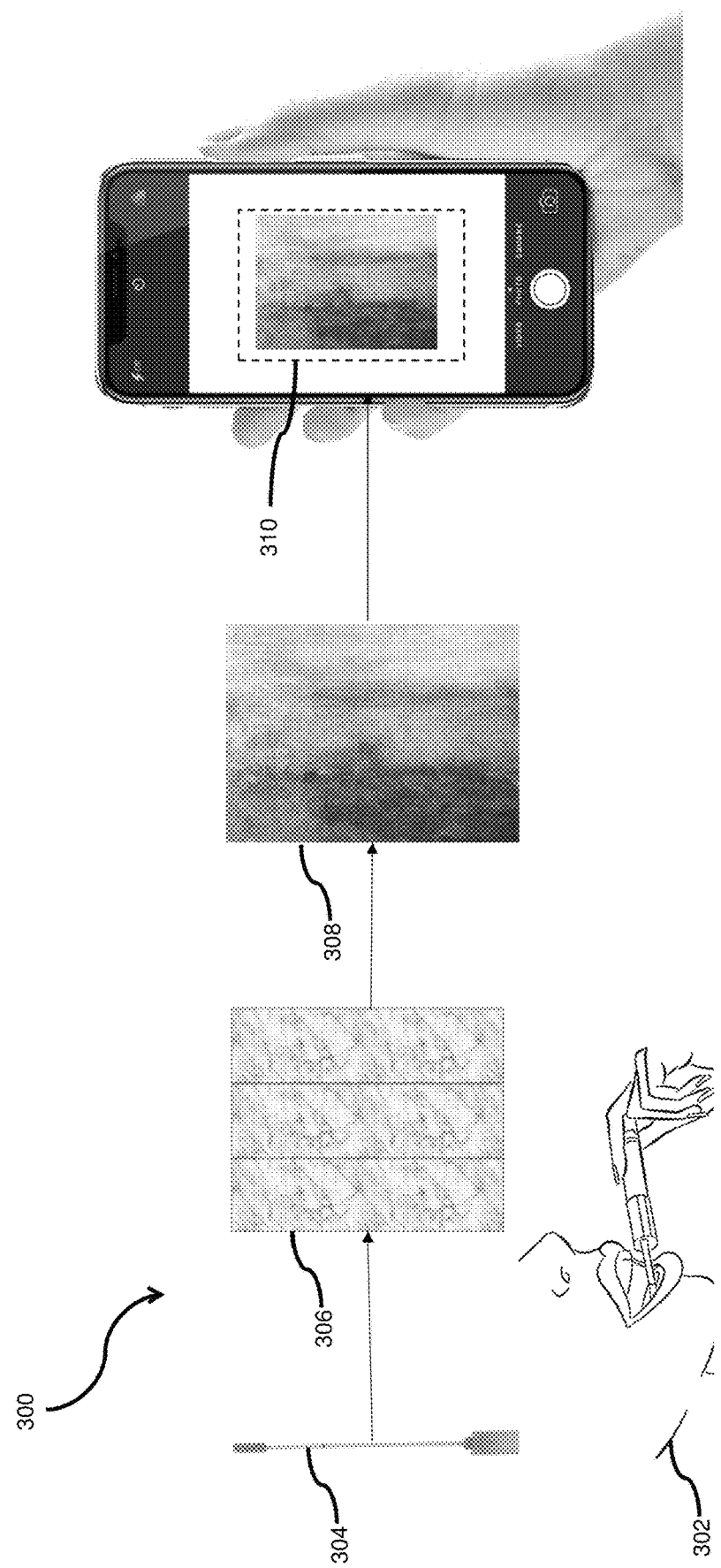
FIG. 3 illustrates a perspective view of receiving the bio-sample from a user, in accordance with at least one embodiment.

The memory 112 is configured to receive bio-sample data of the user through a bio-sample module 208. FIG. 3 illustrates a perspective view of receiving the bio-sample from user 302, in accordance with at least one embodiment. FIG. 3 is explained in conjunction with FIG. 2. The bio-sample module 208 is configured to facilitate user 302 to collect a bio-sample from salivary glands in a form of saliva by using a tool 304 such as a swab. The bio-sample module 208 is configured to facilitate the user to place the bio-sample on a reactant material 306 comprising a plurality of reactant properties pertaining to chemical information of the user's body. The reactant material 306 changes the color (308) upon receiving the bio-sample. In an embodiment, the bio-sample module 208 is configured to facilitate the user to capture an image 310 of the reactant material 306 upon placing the bio-sample to obtain the bio-sample data.

Typically, the microbiome is correlated with depression. The microbiome can furthermore be found in bio-samples. Therefore, salivary bio-samples should have some correlation to rates of mental health. The bio-sample collection process of the present invention does not aim to sequence DNA or genome as may typically be common, but strictly identifies characteristics pertaining to mental health, leads to data that is much more unique and strictly usable for the described purpose herein. The severity of data leakage risks may, therefore, be reduced.

According to an embodiment herein, the user is prompted to collect a bio-sample from the salivary glands in the form of saliva. The bio-sample may be placed on a reactant material. Different parts of the reactant material may have different reactant properties pertaining to different chemical information from the body. Said reactant material may include but is not limited to ketostix strips, API 20E test strips, nitrocellulose-based membranes, glass cellulose-based absorbent pads, pH strips. Fluorescent light may be used to extract data pertaining to different reactant properties of the bio-sample.

In another embodiment of the invention, the bio-sample may be placed into a soluble substance that visually interacts with the bio-sample. Upon successful completion of a bio-sample collection and interaction process, the user is prompted to take an image of the reactive process. Said bio-sample image acquisition process may be done within an application from a handheld electronic device, a computer device equipped with a camera, or any photographic device.

Recent research has furthermore shown that saliva microbiome profiles are minimally affected by collection methods or DNA extraction protocols which may enable bio-sampling of such information from the human body. The image data of the bio-sample is uploaded to the server and combined with other data to provide a final dataset.

The memory 112 is configured to receive dementia type and dementia severity data of the user through a dementia categorization module 208. The type of dementia includes but is not limited to Alzheimer's disease, frontotemporal disorders, Lewy body dementia (LBD), and mixed dementia which is a combination of two or more types of dementia. Typically, dementia is a progressive brain disease that progresses differently in every patient and can be classified based on the symptoms of the patients such as short-term memory lapse, difficulty with complex tasks, poor judgment, increased confusion and frustration, unable to communicate, unable to maintain bodily functions, including walking and eventually swallowing and controlling the bladder, etc.

In an embodiment, the memory 112 is configured to present one or more questions pertaining to the diagnosis of dementia and a plurality of corresponding selectable answers through a questionnaire module. In an embodiment, the questionnaire module facilitates the patient to select at least one answer from the plurality of corresponding selectable answers to the one or more questions to obtain the cognitive assessment data. According to an embodiment herein, the user may furthermore be prompted to answer questions pertaining to the state of their mental health. Such questionnaires may include but are not limited to the Goldberg Depression Questionnaire, PHQ-9 Depression Test, Hamilton Depression Rating Scale (HAD-D), Hamilton Anxiety Rating Scale (HAM-A), Generalized Anxiety Disorder Questionnaire-IV, GAD7 Anxiety test questionnaire or other clinical questionnaire process used to assess mental health. Such questionnaires may furthermore include cognitive assessment tests as well as questionnaires including general questions on the physical state of the user's health. Data may also comprise the progression of mild cognitive impairment.

The memory 112 is configured to transmit a final dataset by compiling the patient data, the bio-sample data, the dementia type, and dementia severity data, and the dementia progression data of the user through a data transmission module 210. The server 102 is communicatively coupled to the memory 112 over the network 106. Server 102 is configured to process the final dataset received from the data transmission module 210 by applying a machine learning module 108.

The machine learning module 108 has been trained to create generative medicines based on the progression of dementia of the user using a generative adversarial neural network (GAN). The GAN comprising one or more Deep Convolutional GANs (DCGANs), one or more Wasserstein GANs (WGANs), and one or more Self-Attention GANs (SAGANs). The server 102 is configured to select, the one or more generative medicines created by the machine learning module, the one or more generative medicines with the highest expected efficacy for treatment or prevention of dementia is selected, or any combination of treatment or prevention of mental health disorders based on the machine learning module. The server 102 is configured to transmit the one or more generative medicines to one or more computing devices 104.

In an embodiment, the final dataset is uploaded to server 102 and analyzed by various machine learning algorithms associated with the machine learning module 108 to generate one or more tailored diets based on the information submitted by the customer or the user. The tailored diets may be medical products produced and shipped directly to the users when complete. Thus, the present computer-implemented method and system provide a diagnostic mechanism as well as supply the tailored diets to the user. In an embodiment, server 102 estimates the toxicity of one or more generative medicines transmitted to the computing device through a toxicity estimation module. In an embodiment, the one or more processors 110 are configured to collect genetic data of the user through a genetic data module 118 in addition to or separate from a bio-sample collection module described herein. Typically, genetic data is related to the inherited or acquired genetic characteristics of the patient which can be obtained from chromosomal, deoxyribonucleic acid (DNA), or ribonucleic acid (RNA) analysis.

In an embodiment, the toxicity may be estimated based on feedback data received from one or more patients after consumption of the created generative medicines. A predictive toxicity model may be trained based on the toxicity feedback data and then a second set of generative medicines may be selected subject to toxicity constraints. In another embodiment, previously existing databases of molecular compositions and toxicity may be used to train the predictive toxicity model. In another embodiment, rodent models of toxicity may be used to estimate toxicity in humans' subjects. In another embodiment, measured toxicity may comprise measuring other adverse effects, in a continuous or binary data format. In another embodiment, patient data pertaining to historical reactions to different medicines and/or current use of medicine may further be incorporated into a toxicity analysis. In an embodiment, patient history data may be analyzed manually and/or through Natural Language Processing and/or other machine learning methods to determine personalized patient toxicity risks.

According to an embodiment herein, the present computer-implemented systems and methods may be extended to other neurodegenerative diseases including but not limited to Parkinson's disease, Prion disease, Motor neurone diseases (MND), Huntington's disease (HD), Spinocerebellar ataxia (SCA) and/or Spinal muscular atrophy (SMA).

According to an embodiment herein, the machine learning module 108 uses machine learning algorithms that may be trained to prioritize the diversity of medical recipes to broaden the number of unique data points that the machine learning algorithms may learn from.

In one embodiment, patient data may be clustered to create fewer categories within the recipe generation process. Examples of such clustering methods include but are not limited to Affinity Propagation, Agglomerative Clustering, BIRCH, DBSCAN, K-Means, Mini-Batch, K-Means, Mean Shift, OPTICS, Spectral Clustering and/or Gaussian Mixture Models.

In one embodiment of the present computer-implemented systems and methods, a sensor-equipped medicine container may be provided to the patient, measuring the weight of the medicine, which may provide indications to what degree the patient is adhering to the treatment plan and at what times the patient has been taking their medicine. The medicine container may furthermore be equipped with an alarm in the form of a sound and/or light, that may be activated to remind the patient to take their medicine at certain points during the day.

In one embodiment of the present computer-implemented systems and methods, generated recipes may contain digestible bio-sensors to signal and track the medication adherence of the patient.

In an embodiment, the bio-sample module 206 is configured to facilitate the user to collect a bio-sample from biological materials including but not limited to blood, urine, tissue, cells, and/or cell cultures.

In an embodiment, the bio-sample module 206 is configured to facilitate the user to place the bio-sample in a container with a soluble substance having one or more reactant properties pertaining to biological information of the user's body.

In an embodiment, the bio-sample module 206 is configured to facilitate the user to place the bio-sample in an airtight container to be preserved and analyzed in a laboratory setting.

Figure 4:
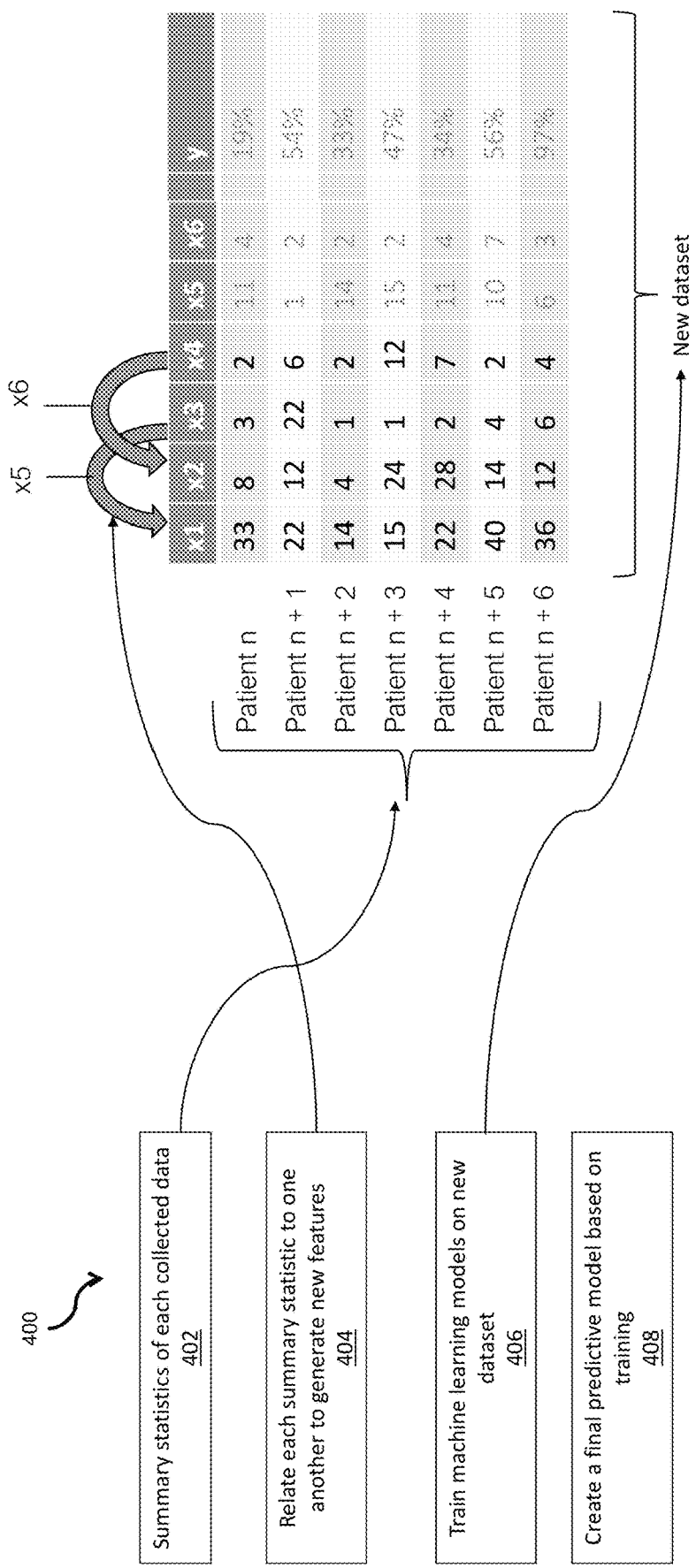
FIG. 4 illustrates a flow diagram of a machine learning training and feature generation through a division of columns by one another, in accordance with at least one embodiment.

FIG. 4 illustrates a flow diagram 400 of a machine learning training and feature generation through a division of columns by one another, in accordance with at least one embodiment. Block 402 depicts the summary statistics of each collected data. Block step 404 depicts how each summary statistic is related to one another to generate new features. At block 406, machine learning models are trained on a new dataset. At block 408, a final predictive model is created based on training. The Y-variable in the column depicts an absolute level of mental health and/or change in mental health and/or the efficacy of a medical product.

In an embodiment, the machine learning model is trained to predict the effects of certain medicines on mental health progression. Based on the collected data, a final dataset may be created by combining the collected data from the user in previous steps with the recipes that were given to the user.

This dataset, which may be construed as the 'x-variables', may then be combined with data pertaining to the mental health progression of each patient, this may be construed as the 'y-variable' in the machine learning process. Said mental health progression data of each patient may be collected one or more weeks after the patient has been given their medicine. The machine learning methods may include but are not limited to decision tree-based machine learning methods, artificial neural networks, convolutional neural networks, logistic regression, naive Bayes, nearest neighbor, support vector machines, boosted tree learning methods, and/or generative neural networks.

Dementia progression data may include mental function tests, cognitive assessment tests, blood sample analysis, eye retina scans, speech analysis, structural MRI scans, functional MRI scans, PET-scans, cerebrospinal fluid data, EEG data, cerebral blood flow data, brain metabolism data, human head image data, motor function data. Dementia progression data may further include any data indicative of the presence or stage of proteins indicative of dementia. Such proteins may include but are not limited to, Amyloid beta, alpha-synuclein and tau.

Figure 5:
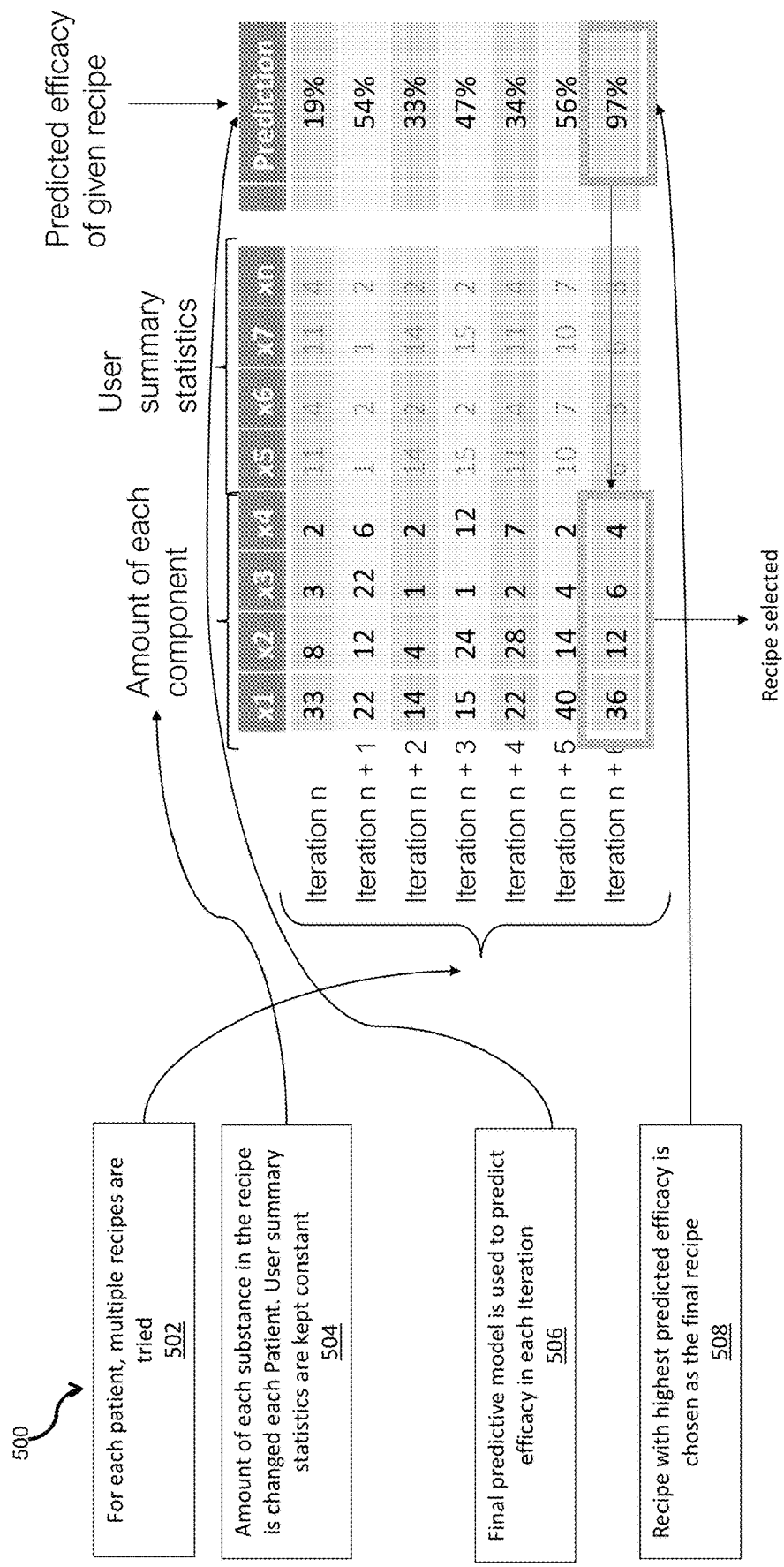
FIG. 5 illustrates a flow diagram of generating the tailored medical recipes, in accordance with at least one embodiment.

FIG. 5 illustrates a flow diagram 500 of generating the tailored medical recipes, in accordance with at least one embodiment. Block 502 depicts that for each patient, multiple recipes (medical recipes) may be tried. Block 504 depicts the amount of each substance in the medical recipe is changed for each patient and the user summary statistics are kept constant. At block 506, the final predictive model is used to predict efficacy in each iteration. At block 508, the medical recipe with the highest predicted efficacy is chosen as a final medical recipe for the user.

In an embodiment, for each patient recipes are created and the recipe, or any data transformation function such as average, median, or sum, of several recipes, with the highest, predicted efficacy, may be selected as the final recipe to be produced for the patient.

A solving system may be employed, subject to physical constraints to doses of each variable, to generate a vast number of potential recipes based on the pre-trained model's predicted efficacy as the maximization goal. Such solving systems may include brute force search algorithms and/or may include but are not limited to linear solving methods and/or non-linear solving methods such as genetic algorithm solvers and/or random number generators and/or particle swarm methods. In this process, the data collected from the user is held constant, while values for each possible component in the recipe are tailored. Such solving systems may furthermore include optimization algorithms such as non-differential objective function optimization algorithms. The algorithms include: Direct algorithms, stochastic algorithms and population algorithms. These algorithms may be employed in more challenging objective problems that may have noisy function evaluations and several global optima. This may be in cases where finding a good or good enough solution is challenging or infeasible using other methods. This can add robustness to the search and increase the likelihood of overcoming local optima.

In an embodiment, the risk of generated medicines being overfit or that lack generalizability may be determined using a machine learning model that has been trained to discriminate between "good" and "bad" estimations of high efficacy. Such a discriminator model may be trained on examples of datasets with a high predicted efficacy and varying degrees of realised efficacy. These datasets may be specific to a generative medicine context or may be general datasets from other fields of study.

Certain constraints may be imposed on solving methods. Examples of constraints may include total recipe amounts in terms of weight, several different compounds/substances included, for example, a certain minimum or maximum amount per compound that is allowed to be included in the recipe, as well as certain combinations of substances that may be deemed inappropriate.

Substances that may be included in the recipe generation process may include but are not limited to any natural health product or naturally-occurring substance. Said products may include but is not limited to *Ginkgo Biloba*, Ketogenic Diet, Sulforaphane, Genistein, Ketogenic medium-chain triglyceride drink (MCT drink), Mediterranean Diet, Low-fat Diet, MMFS-205-SR, Omega-3 treatment, MitoQ, EGCG, melatonin, Probiotic supplemented intervention, HYMN Ketone Esther drink, Grape Powder, Meganatural-Az Grapeseed Extract, vitamin E in combination with Selegiline and any of Vitamins A-K and Carotenoids. It may furthermore include different doses of certified mental health medicines such as selective serotonin reuptake inhibitors (SSRIs), serotonin-norepinephrine reuptake inhibitors (SNRIs), atypical antidepressants such as bupropion (Wellbutrin XL, Wellbutrin SR, Aplenzin, Forfivo XL), mirtazapine (Remeron), nefazodone, trazodone and vortioxetine (Trintellix), tricyclic antidepressants and/or monoamine oxidase inhibitors (MAOIs). It may furthermore include any prescription medicine available.

In an embodiment, a generative adversarial neural networks (GANs) approach may be employed to generate potential recipes based on the data submitted by the user. Such GANs may include Deep Convolutional GANs (DC-GANs), Wasserstein GANs (WGANs), Self-Attention GANs (SAGANs), and BigGANs. Variational autoencoders may furthermore be used in the training process. Such methods may be useful in overcoming the overfitting of the data.

In an embodiment, follow up information from the user may be collected, which may enable the analysis of the metadata associated with the predicted recipes that were made. In one embodiment, in future variations of the recipe, one may compare how well the predicted recipes performed in real life, and adjust future predictions arising from the machine learning model to create new recipes accordingly, taking this adjustment factor into account.

In an embodiment, placebo effects pertaining to the trial may be analyzed and progression data may be adjusted for these effects to improve future recipe generation.

In an embodiment, the software application may provide the option of connecting via voice and/or video interaction and/or offering psychotherapeutic methods including but not limited to cognitive behavioral therapy, psychoanalysis and psychosynthesis to the user. In an embodiment, such communication may be performed through an automated response system driven by artificial intelligence including examples such as chatbots.

Figure 6:
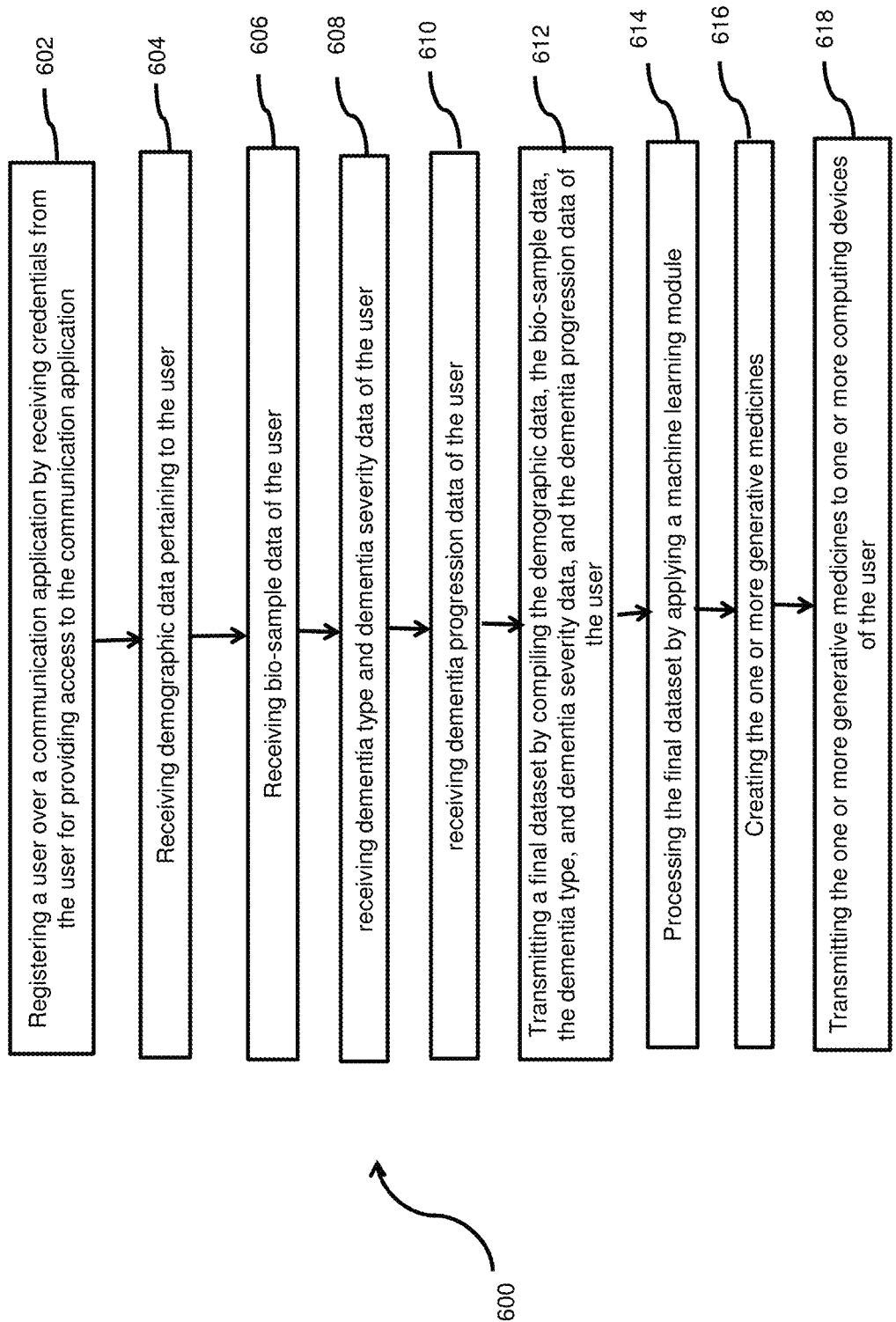
FIG. 6 illustrates a flowchart of the computer-implemented method for creating generative medicines for dementia, in accordance with an alternative embodiment of the present invention.

FIG. 6 illustrates a flowchart 600 of the computer-implemented method for creating generative medicines for dementia, in accordance with an alternative embodiment of the present invention. The computer-implemented method includes step 602 of registering a user over a communication application by receiving one or more credentials from the user for providing access to the communication application through a registration module. In an embodiment, the communication application is executable on one or more computing devices of the user. The computer-implemented method includes step 604 of receiving patient data of a user through a patient data module. The computer-implemented method includes step 606 of receiving bio-sample data of the user through a bio-sample module. In an embodiment, the bio-sample module is configured to facilitate the user to collect a bio-sample from salivary glands in a form of saliva. In an embodiment, the bio-sample module is configured to facilitate the user to place the bio-sample on a reactant material having one or more reactant properties pertaining to chemical information of the user's body. In an embodiment, the bio-sample module is configured to facilitate the user to capture an image of the reactant material upon placing the bio-sample to obtain the bio-sample data.

The computer-implemented method includes step 608 of receiving dementia type and dementia severity data of the user through a dementia categorization module. The computer-implemented method includes step 610 of transmitting a final dataset by compiling the patient data, the bio-sample data, the dementia type and dementia severity data of the user through a data transmission module. The computer-implemented method includes step 612 of processing the final dataset received from the data transmission module over a network by applying a machine learning module to the final dataset. In an embodiment, the one or more processors are configured to collect genetic data of the user through a genetic data module. The machine learning module has been trained to create generative medicines based on the progression of dementia of the user using a generative adversarial neural network (GAN). The GAN includes Deep Convolutional GANs (DCGANs), one or more Wasserstein GANs (WGANs), and one or more Self-Attention GANs (SAGANs). The computer-implemented method includes a step 614 of selecting the one or more generative medicines created by the machine learning module with the highest expected efficacy for treatment or prevention of dementia, or any combination of treatment or prevention of mental health disorders based on the machine learning module. The computer-implemented method includes a step 616 of transmitting the generative medicines to one or more computing devices.

In an embodiment, the server estimates the toxicity of one or more generative medicines transmitted to the computing device through a toxicity estimation module.

In an embodiment, the computer-implemented method includes a step of selecting, the one or more generative medicines with the highest predicted efficacies on the progression of dementia of the user. In an embodiment, the computer-implemented method includes a step of transmitting, by the server, the one or more generative medicines to one or more computing devices of the user.

The present computer-implemented system and method can be utilized in modern technology to make personalized medicine services affordable and accurate. Further, the present computer-implemented system and method may focus on reversing the build-up of proteins believed to be important factors in affecting the disease. Furthermore, the present computer-implemented system and method may further focus on restoring important memory functions and/or improving the general wellbeing of patients affected by dementia.

The present computer-implemented system and method may be applied in other diseases where drug discovery may have failed and where there is little clarity into disease pathology and/or there are few successful molecules for machine learning algorithms to learn from.

In some embodiment of the present computer-implemented system and method, in an absence of physical clinical sites, the trial may be conducted in a decentralized fashion and medicine may be provided directly to the patients.

In some embodiments, the observed placebo effects in each randomized treatment groups may be used to approximate the measurement error effect present in the study to arrive at more accurate measurements of efficacy.

Unless otherwise defined, all terms (including technical and scientific terms) used in this disclosure have the same meaning as commonly understood by one of ordinary skill in the art to which this disclosure belongs. It is to be understood that the phrases or terms employed of the present invention is for description and not of limitation. As will be appreciated by one of skill in the art, the present disclosure may be embodied as a device, system, and method or computer program product. Further, the present invention may take the form of a computer program product on a computer-readable storage medium having computer-usable program code embodied in the medium. The present systems and methods have been described above with reference to specific examples. However, other embodiments and examples than the above description are equally possible within the scope of the present invention. The scope of the disclosure may only be limited by the appended patent claims. Even though modifications and changes may be suggested by the persons skilled in the art, it is the intention of the inventors and applicants to embody within the patent warranted heron all the changes and modifications as reasonably and properly come within the scope of the contribution the inventors and applicants to the art. The scope of the embodiments of the present invention is ascertained with the claims to be submitted at the time of filing the complete specification.

What is claimed is:

1. A computer-implemented method for creating one or more generative medicines for dementia, the computer-implemented method comprising:
registering, by one or more processors, a user over a communication application by receiving one or more credentials from the user for providing access to the communication application through a registration module;
receiving, by the one or more processors, patient data of the user inputted by the user through a patient data module;
receiving, by the one or more processors, bio-sample data of the user inputted by the user through a bio-sample module;
receiving, by the one or more processors, dementia type and dementia severity data of the user through a dementia categorization module;
transmitting, by the one or more processors, a final dataset by compiling the patient data, the bio-sample data, the dementia type and the dementia severity data of the user through a data transmission module;
processing, by a server, the final dataset by applying a machine learning module to the final dataset received from the data transmission module over a network, wherein the machine learning module has been trained to create generative medicines based on the progression of dementia of the user using a generative adversarial neural network (GAN), wherein the GAN comprises one or more Deep Convolutional GANs (DCGANs), one or more Wasserstein GANs (WGANs), and one or more Self-Attention GANs (SAGANs);
selecting, by the server, the one or more generative medicines created by the machine learning module with the highest expected efficacy for treatment or prevention of dementia, or any combination of treatment or prevention of mental health disorders based on the machine learning module; and transmitting, by the server, the one or more generative medicines to one or more computing devices, wherein the bio-sample module is configured to facilitate the user to capture an image of a reactant material upon placing a bio-sample to obtain the bio-sample data.

2. The computer-implemented method of claim 1, wherein the bio-sample module is configured to facilitate the user to collect a bio-sample from salivary glands in a form of saliva.

3. The computer-implemented method of claim 1, wherein the bio-sample module is configured to facilitate the user to place the bio-sample on a reactant material having one or more reactant properties pertaining to chemical information of the user's body.

4. The computer-implemented method of claim 1, wherein the communication application is executable on the one or more computing devices of the user.

5. The computer-implemented method of claim 1, wherein the server generates one or more tailored diets based on the final dataset processed by the machine learning module.

6. The computer-implemented method of claim 1, wherein the server estimates toxicity of the one or more generative medicines transmitted to the computing device through a toxicity estimation module.

7. The computer-implemented method of claim 1, wherein the one or more processors are configured to collect genetic data of the user through a genetic data module.

8. The computer-implemented method of claim 1, wherein the one or more processors are configured to collect neuronal activity data of the user through a neuronal activity module.

9. The neuronal activity module of claim 8, wherein the neuronal activity module is configured to facilitate the user to collect neuronal activity data in a form of an EEG reading.

10. The computer-implemented method of claim 1, wherein the image is acquired from a handheld electronic device, a computer device equipped with a camera, or any photographic device of the user.

11. A computer-implemented system for creating one or more generative medicines for dementia, the system comprising:
a processor;
a memory communicatively coupled to the processor, wherein the memory stores instructions executed by the processor, wherein the memory is configured to:
register a user over a communication application by receiving one or more credentials from the user for providing access to the communication application through a registration module;
receive patient data of a user inputted by the user through a patient data module;
receive bio-sample data of the user inputted by the user through a bio-sample module;
receive dementia type and dementia severity data of the user through a dementia categorization module; and
transmit a final dataset by compiling the patient data, the bio-sample data, the dementia type and the dementia severity data of the user through a data transmission module;
a server communicatively coupled to the memory over a network, wherein the server is configured to:

process the final dataset received from the data transmission module over a network by applying a machine learning module, wherein the machine learning module has been trained to create generative medicines based on the progression of dementia of the user using a generative adversarial neural network (GAN), wherein the GAN comprising one or more Deep Convolutional GANs (DCGANs), one or more Wasserstein GANs (WGANs), and one or more Self-Attention GANs (SAGANs);

select, the one or more generative medicines created by the machine learning module, the one or more generative medicines with the highest expected efficacy for treatment or prevention of dementia is selected, or any combination of treatment or prevention of mental health disorders based on the machine learning module; and transmit the one or more generative medicines to one or more computing devices, wherein the bio-sample module is configured to facilitate the user to capture an image of a reactant material upon placing a bio-sample to obtain the bio-sample data.

12. The computer-implemented system of claim 11, wherein the bio-sample module is configured to facilitate the user to collect a bio-sample from salivary glands in a form of saliva.

13. The computer-implemented system of claim 11, wherein the bio-sample module is configured to facilitate the user to place the bio-sample on a reactant material having one or more reactant properties pertaining to chemical information of the user's body.

14. The computer-implemented system of claim 11, wherein the communication application is executable on the one or more computing devices of the user.

15. The computer-implemented system of claim 11, wherein the server is configured to generate one or more tailored diets based on the final dataset processed by the machine learning module.

16. The computer-implemented system of claim 11, wherein the server is configured to estimate toxicity of the one or more generative medicines transmitted to the computing device through a toxicity estimation module.

17. The computer-implemented system of claim 11, wherein the one or more processors are configured to collect genetic data of the user through a genetic data module.

18. The computer-implemented system of claim 11, wherein the one or more processors are configured to collect neuronal activity data of the user through a neuronal activity data module.

19. A computer-implemented method for creating one or more generative medicines for dementia, the computer-implemented method comprising:
registering, by one or more processors, a user over a communication application by receiving one or more credentials from the user for providing access to the communication application through a registration module;
receiving, by the one or more processors, patient data of the user inputted by the user through a patient data module and bio-sample data of the user inputted by the user through at least one bio-sample module;
transmitting, by the one or more processors, a final dataset by compiling the data related to the user through a data transmission module;
processing, by a server, the final dataset received from the data transmission module over a network by applying a machine learning module, wherein the machine learning module is configured to generate features from the final dataset by interrelating the user's data and the generative medicine data;

creating, by the server, the one or more new generative medicines based on the processed dataset by the machine learning module, wherein the server creates the generative medicines for treatment or prevention of dementia, or any combination of treatment or prevention of dementia based on the final dataset processed by the machine learning module, wherein the machine learning module has been trained to predict the progression of dementia and is configured to generate a new dataset by adjusting the medical recipe values in each generative medicine using an optimization algorithm that optimizes for values that generate the highest predicted efficacy by the machine learning module, wherein the server employs an optimization algorithm to create the generative medicines based on the user's data, wherein the optimization algorithm comprises one or more population algorithms, direct algorithms and stochastic algorithms;

selecting, the one or more generative medicines with the highest predicted efficacies on the progression of dementia of the user; and transmitting, by the server, the one or more generative medicines to one or more computing devices of the user, wherein the bio-sample module is configured to facilitate the user to capture an image of a reactant material upon placing a bio-sample to obtain the bio-sample data, and the image is acquired from a handheld electronic device, a computer device equipped with a camera, or any photographic device of the user.

20. The computer-implemented method of claim 19, wherein receiving, by the one or more processors, the patient data includes receiving, by the one or more processors, at least one of or any combination of:
   mental health questionnaire data from the user inputted by the user through a questionnaire module.

21. The computer-implemented method of claim 19, wherein transmitting, by the one or more processors, the final dataset by compiling the data related to the user through a data transmission module includes compiling the one of or any combination of the bio-sample data, and the mental health questionnaire data of the user through the data transmission module.

22. The computer-implemented method of claim 19, wherein the one or more transmitted generative medicines are produced and sent to the user.

23. The computer-implemented method of claim 19, where each generative medicine's likelihood of overfitting is predicted by using a discriminator machine learning model.

24. The computer-implemented method of claim 19, wherein receiving, by the one or more processors, the patient data includes receiving, by the one or more processors, at least one of or any combination of:
   neuronal activity data of the user through at least one neuronal activity module.

25. The computer-implemented method of claim 19, further comprising training the machine learning module with a variational autoencoder.

26. The computer-implemented method of claim 25, wherein the variational autoencoder reduces overfitting of the data.

* * * * *